(12) United States Patent
Taylor et al.

(10) Patent No.: US 7,682,421 B2
(45) Date of Patent: Mar. 23, 2010

(54) DEGASSING A LIQUID USING A GRAVITY FED APPARATUS

(75) Inventors: Gareth P. Taylor, Indian Trial, NC (US); Jorge Munoz, Pineville, NC (US)

(73) Assignee: Celgard LLC, Charlotte, NC (US)

( * ) Notice: Subject to any disclaimer, the term of this patent is extended or adjusted under 35 U.S.C. 154(b) by 651 days.

(21) Appl. No.: 11/548,713

(22) Filed: Oct. 12, 2006

(65) Prior Publication Data

US 2008/0087164 A1    Apr. 17, 2008

(51) Int. Cl.
*B01D 19/00* (2006.01)
(52) U.S. Cl. .................................. 95/46; 96/6
(58) Field of Classification Search ...... 95/46; 96/6; 604/126
See application file for complete search history.

(56) References Cited

U.S. PATENT DOCUMENTS

| | | | |
|---|---|---|---|
| 3,631,654 A * | 1/1972 | Riely et al. ................. | 96/6 |
| 5,186,832 A | 2/1993 | Mancusi et al. | |
| 5,264,171 A | 11/1993 | Prasad et al. | |
| 5,284,584 A | 2/1994 | Huang et al. | |
| 5,352,361 A | 10/1994 | Prasad et al. | |
| 5,695,545 A * | 12/1997 | Cho et al. .................... | 95/46 |
| 6,267,926 B1 | 7/2001 | Reed et al. | |
| 6,336,916 B1 * | 1/2002 | Bormann et al. ............ | 604/251 |
| 6,402,818 B1 | 6/2002 | Sengupta | |
| 6,503,225 B1 * | 1/2003 | Kirsch et al. ................ | 604/126 |
| 6,558,450 B2 * | 5/2003 | Sengupta et al. ............ | 95/46 |
| 6,616,841 B2 | 9/2003 | Cho et al. | |
| 6,790,262 B2 | 9/2004 | Sengupta et al. | |
| 2005/0194305 A1 | 9/2005 | Vido et al. | |
| 2005/0218064 A1 | 10/2005 | Sengupta et al. | |
| 2006/0081524 A1 | 4/2006 | Sengupta et al. | |
| 2007/0278145 A1 * | 12/2007 | Taylor et al. ............ | 210/321.6 |

OTHER PUBLICATIONS

U.S. Appl. No. 11/043,351, filed Jan. 26, 2006.
U.S. Appl. No. 11/447,188, filed Jun. 5, 2005.

* cited by examiner

*Primary Examiner*—Duane Smith
*Assistant Examiner*—Douglas J Theisen
(74) *Attorney, Agent, or Firm*—Hammer & Associates, P.C.

(57) ABSTRACT

A liquid is degassed with an apparatus including a membrane contactor, where the liquid is drawn through the apparatus by gravity.

18 Claims, 2 Drawing Sheets

DEGASSING A LIQUID USING A GRAVITY FED APPARATUS

FIELD OF THE INVENTION

The invention is directed to degassing a liquid using a gravity fed apparatus including a membrane contactor.

BACKGROUND OF THE INVENTION

Degassing a liquid using a membrane contactor is known. See: U.S. Pat. Nos. 6,790,262, 6,558,450, 6,503,225, 6,402,818, 6,267,926, 6,616,841, 5,695,545, 5,352,361, 5,284,584, 5,264,171, and 5,186,832; U.S. Patent Publications Nos. 20050194305, 20050218064, and 20060081524; and U.S. patent application Ser. No. 11/043,351 filed Jan. 26, 2006 and Ser. No. 11/447,188 filed Jun. 5, 2005.

However, degassing a liquid where the liquid is gravity-fed to the contactor is not known. Typically, the liquid is pumped to the contactor.

In U.S. Pat. No. 6,503,225, intravenous fluid is de-bubbled by use of a lumen-side liquid flow contactor where the intravenous fluid is gravity fed to the contactor.

There is a need for an apparatus and a method for degassing a liquid where the liquid is gravity-fed to the membrane contactor.

SUMMARY OF THE INVENTION

A liquid is degassed with an apparatus including a membrane contactor, where the liquid is drawn through the apparatus by gravity.

DESCRIPTION OF THE DRAWINGS

For the purpose of illustrating the invention, there is shown in the drawings a form that is presently preferred; it being understood, however, that this invention is not limited to the precise arrangements and instrumentalities shown.

DESCRIPTION OF THE INVENTION

Figure 1:
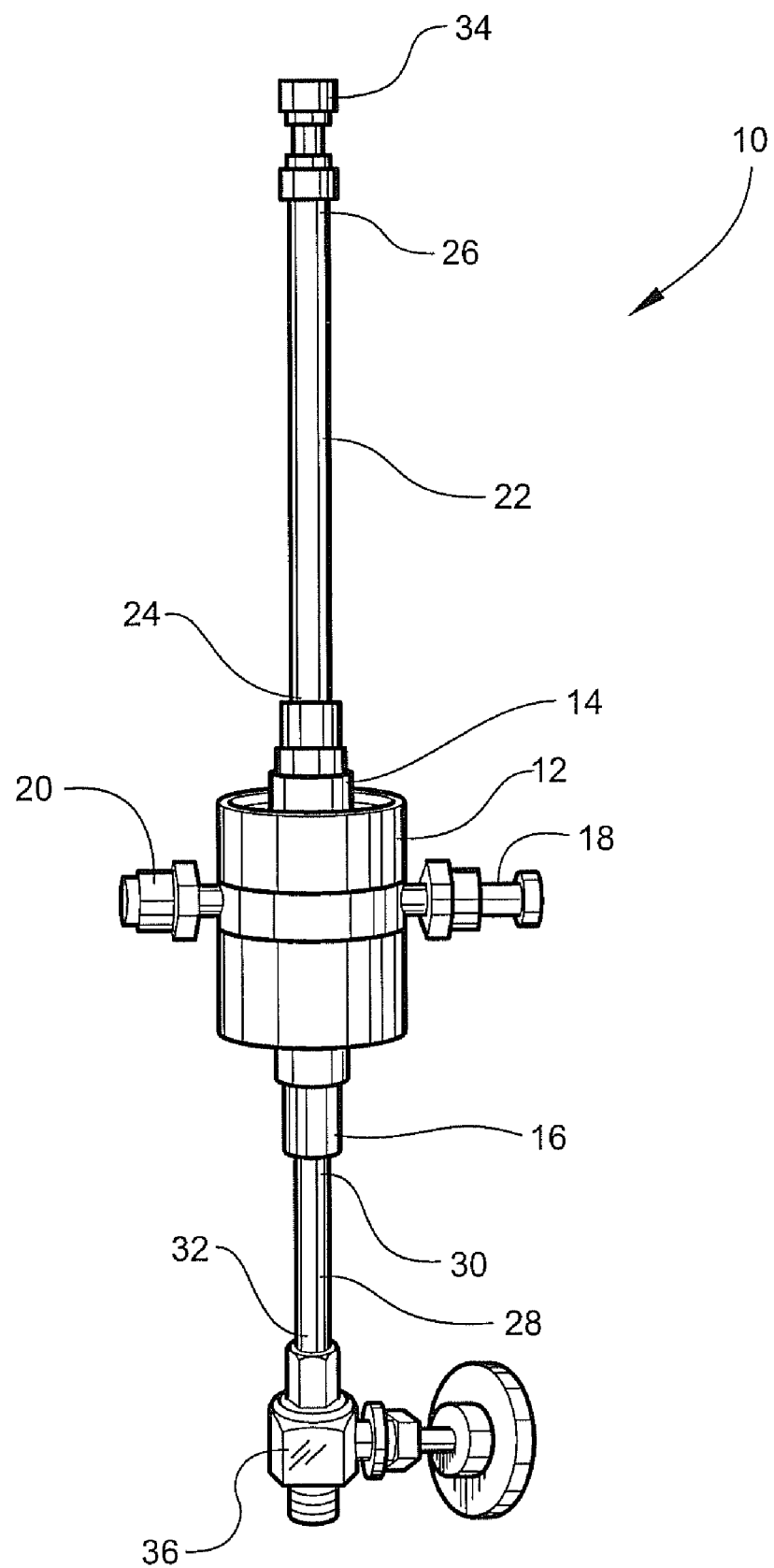
FIG. 1 illustrates a first embodiment of the present invention.

Referring to the drawings, wherein like numerals indicate like elements, there is shown in FIG. 1 a first embodiment of the present invention, an apparatus for degassing a liquid 10, where the liquid is gravity fed to the apparatus.

Apparatus 10 generally comprises a membrane contactor 12, a first tube 22, and a second tube 28. In the embodiment shown in FIG. 1, the apparatus additionally includes an optional flow regulating mechanism 36 operatively associated with the second tube 28. In the embodiment shown in FIG. 2, the apparatus 10' additionally includes an optional flow regulating mechanism 36 operatively associated with the first tube 22.

Figure 2:
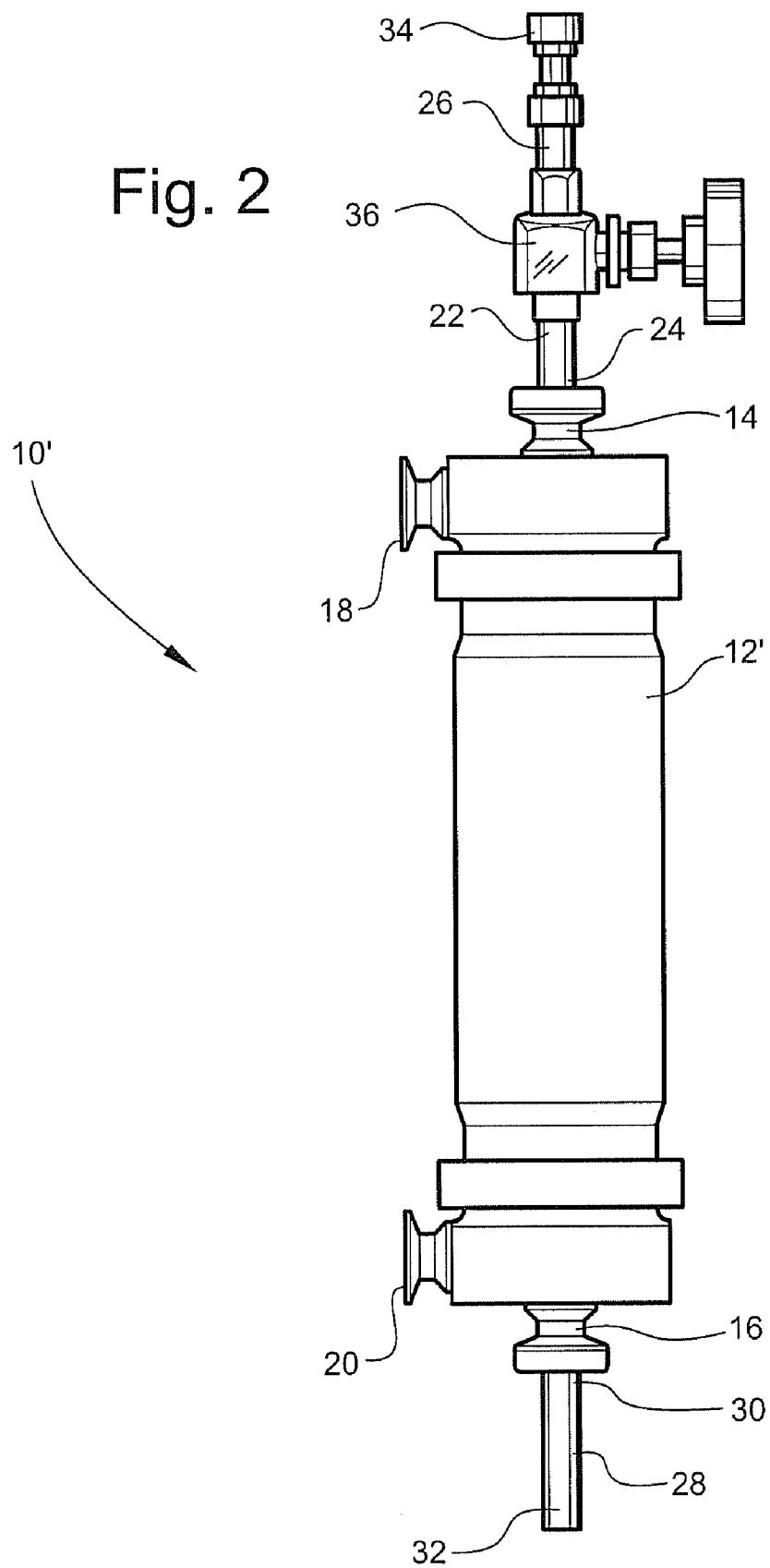
FIG. 2 illustrates a second embodiment of the present invention.

Membrane contactor 12 may be a membrane contactor used to degas a liquid. Such membrane contactors may have flat sheet membranes or hollow fiber membranes. In the embodiments shown in FIGS. 1 and 2, the membrane contactors are shell-side liquid flow hollow fiber contactors. In FIG. 1, the hollow fibers are oriented in the radial direction of the contactor 12 (i.e., transverse flow). For example, see: U.S. patent application Ser. No. 11/043,351 filed Jan. 26, 2006 and Ser. No. 11/447,188 filed Jun. 5, 2005, incorporated herein by reference. In FIG. 2, the hollow fibers are oriented in the longitudinal direction of the contactor 12' (i.e., radial flow). For example, see: U.S. Pat. Nos. 6,790,262, 6,558,450, 6,503,225, 6,402,818, 6,267,926, 6,616,841, 5,695,545, 5,352,361, 5,284,584, 5,264,171, and 5,186,832, U.S. Patent Publications Nos. 20050194305, 20050218064, and 20060081524, each incorporated herein by reference.

Membrane contactor 12 and 12' additionally have a liquid inlet 14, a liquid outlet 16, a vacuum port 18, and an auxiliary port 20. Generally, membrane contactors have a 'shell-side' and a 'lumen-side' (not shown). The shell-side and the lumen-side are discrete chambers within the contactor that are separated from one another by a membrane. In the degassing operation, the liquid is confined to the shell-side, while vacuum or vacuum/sweep gas are confined to the lumen-side. A diffusion driving force, e.g., a pressure differential or a concentration gradient, is established between these chambers, so that a component of the liquid, e.g., gas is driven across the membrane by principles quantified by diffusion. The inlet 14 and the outlet 16 may be operatively associated with the shell-side. The vacuum port 18 and the auxiliary port 20 may be operatively associated with the lumen-side.

A first tube 22 has a proximal end 24 and distal end 26. The proximal end 24 is connected to the inlet 14 of the contactor 12. The connection may be either a permanent connection or a removable connection that would allow the tube 22 and the contactor 12 to be easily separated. Such connections are well known. Tube 22 may be flexible or rigid. Flexible tubes would include any conventionally know plastic tubing.

A reservoir connector 34 is located at the distal end of the first tube 22. Reservoir connector 34 is adapted to connect apparatus 12 or 12' with a reservoir of liquid having an entrained gas (not shown). Connector 34 is conventional. The reservoir is any liquid storage device. The reservoir may be a tank, a funnel, or a cylinder.

A second tube 28 has a proximal end 30 and a distal end 32. The proximal end 30 is connected to the outlet 16 of the contactor 12. The connection may be either a permanent connection or a removable connection that would allow the tube 28 and the contactor 12 to be easily separated. Such connections are well known. Tube 28 may be flexible or rigid. Flexible tubes would include any conventionally known plastic tubing.

A flow regulating mechanism 36, which may be operatively associated with either the first tube 22 or the second tube 28, is adapted to control liquid flow to or from the contactor. Flow regulating mechanism 36 may be an orifice or a valve. The valve may be any conventional valve. The valve may be a gate valve, ball valve, needle valve, globe valve, diaphragm valve, and butterfly valve.

In operation, apparatus 10/10' is connected to a reservoir (not shown), so that the apparatus is below the liquid contained in the reservoir. This placement is necessary so that sufficient head pressure is obtained to force the liquid through the membrane contactor 12/12' of the apparatus 10/10'. The membrane contactor 12/12' is connected to a source of vacuum or vacuum/sweep gas via vacuum port 18 or ports 18/20. If used, the flow regulation mechanism 36 (e.g., a valve) is opened. Then, the liquid, entrained with gas, flow through the contactor 12/12', while the vacuum or vacuum/sweep gas is operational. Then, the entrained gas is removed from the liquid. The degassed liquid exits the apparatus via the distal end of the second tube.

The present invention may be embodied in other forms without departing from the spirit and the essential attributes thereof, and, accordingly, reference should be made to the appended claims, rather than to the foregoing specification, as indicated the scope of the invention.

We claim:

1. An apparatus for degassing a liquid comprising:
   a shell-side liquid flow membrane contactor having a liquid inlet, a liquid outlet, and a vacuum port,
   a first tube having a proximal end and a distal end, said proximal end of said first tube being connected to said liquid inlet of said membrane contactor,
   a reservoir connector being connected to said distal end of said first tube, and
   a second tube having a proximal end and a distal end, said proximal end of said second tube being connected to said liquid outlet of said membrane contactor,
   wherein, during use, said distal end of said first tube being positioned above said membrane contactor and said distal end of said second tube being positioned below said membrane contactor, whereby liquid being drawn through said membrane contactor by gravity.

2. The apparatus of claim 1 further comprising a flow regulating mechanism being operatively associated with either said first tube or said second tube.

3. The apparatus of claim 2 wherein said flow regulating mechanism being operatively associated with said first tube.

4. The apparatus of claim 2 wherein said flow regulating mechanism being operatively associated with said second tube.

5. The apparatus of claim 2 wherein said flow regulating mechanism being a valve selected from the group consisting of: gate valves, ball valves, needle valves, globe valves, diaphragm valves, and butterfly valves.

6. The apparatus of claim 1 further comprising a reservoir connected to said reservoir connector.

7. The apparatus of claim 6 wherein said reservoir being selected from the group consisting of: a tank, a funnel, and a cylinder.

8. The apparatus of claim 1 wherein said membrane contactor having either a transverse flow or a radial flow.

9. The apparatus of claim 1 wherein said membrane contactor further having an auxiliary port.

10. The apparatus of claim 9 wherein said vacuum port and said auxiliary port being operatively associated with a lumen-side of said membrane contactor.

11. A method of degassing a liquid comprising the steps of:
    gravity-feeding a liquid containing an entrained gas to an apparatus for degassing the liquid, the apparatus having a shell-side liquid flow membrane contactor,
    degassing the liquid containing the entrained gas by operation of diffusion of the entrained gas across a membrane of the apparatus, and
    discharging a liquid having less entrained gas than the liquid containing the entrained gas from the apparatus.

12. The method of claim 11 wherein degassing comprising providing a vacuum to the apparatus.

13. The method of claim 11 wherein degassing comprising providing a vacuum and a sweep gas to the apparatus.

14. The method of claim 11 wherein the apparatus for degassing a liquid comprising:
    a membrane contactor having a liquid inlet, a liquid outlet, and a vacuum port,
    a first tube having a proximal end and a distal end, said proximal end of said first tube being connected to said liquid inlet of said membrane contactor,
    a reservoir connector being connected to said distal end of said first tube, and
    a second tube having a proximal end and a distal end, said proximal end of said second tube being connected to said liquid outlet of said membrane contactor,
    wherein, during use, said distal end of said first tube being positioned above said membrane contactor and said distal end of said second tube being positioned below said membrane contactor.

15. The method of claim 14 wherein the apparatus further comprising a flow regulating valve being operatively associated with either said first tube or said second tube.

16. The method of claim 15 wherein the apparatus having either a transverse flow or a radial flow.

17. The method of claim 14 wherein said membrane contactor further having an auxiliary port.

18. The method of claim 17 wherein said vacuum port and said auxiliary port being operatively associated with a lumen-side of said membrane contactor.

* * * * *